US010776454B2

United States Patent
Fong et al.

(10) Patent No.: US 10,776,454 B2
(45) Date of Patent: Sep. 15, 2020

(54) DATA CAPTURE AND ROUTING SYSTEM AND METHOD

(75) Inventors: Winston Richard Fong, Auckland (NZ); Benjamin Wilson Casse, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 501 days.

(21) Appl. No.: 14/128,511

(22) PCT Filed: Jun. 26, 2012

(86) PCT No.: PCT/NZ2012/000106
§ 371 (c)(1),
(2), (4) Date: Mar. 19, 2014

(87) PCT Pub. No.: WO2013/002650
PCT Pub. Date: Jan. 3, 2013

(65) Prior Publication Data
US 2014/0207476 A1   Jul. 24, 2014

Related U.S. Application Data

(60) Provisional application No. 61/501,641, filed on Jun. 27, 2011.

(51) Int. Cl.
*G06F 19/00* (2018.01)
*H04L 12/24* (2006.01)
(Continued)

(52) U.S. Cl.
CPC ..... *G06F 19/3456* (2013.01); *A61M 16/0069* (2014.02); *A61M 16/024* (2017.08);
(Continued)

(58) Field of Classification Search
CPC .............. G06F 19/3456; G06F 19/328; A61M 16/0069; A61M 16/0051;
(Continued)

(56) References Cited

U.S. PATENT DOCUMENTS

| 8,126,729 B2 | 2/2012 | Dicks et al. |
| 2002/0023172 A1* | 2/2002 | Gendron ............... G06F 19/321 709/238 |

(Continued)

OTHER PUBLICATIONS

Extended European Search Report for PCT/NZ2012/000106 dated Nov. 4, 2015.
(Continued)

*Primary Examiner* — Vivek D Koppikar
*Assistant Examiner* — Minnah Seoh
(74) *Attorney, Agent, or Firm* — Knobbe, Martens, Olson & Bear, LLP

(57) ABSTRACT

A computer system for routing breathing apparatus compliance data that includes a processor and network interface configured to receive input data including breathing apparatus compliance data via a network, format the compliance data into a destination format in accordance with formatting data and transmit the formatted compliance data via a network to a recipient system in accordance with routing information.

4 Claims, 12 Drawing Sheets

(51) Int. Cl.
*A61M 16/00* (2006.01)
*A61M 16/16* (2006.01)

(52) U.S. Cl.
CPC ........ *G06F 19/328* (2013.01); *H04L 41/0803* (2013.01); *A61M 16/16* (2013.01); *A61M 16/161* (2014.02); *A61M 2016/0027* (2013.01); *A61M 2016/0039* (2013.01); *A61M 2205/3553* (2013.01); *A61M 2205/3561* (2013.01); *A61M 2205/3584* (2013.01); *A61M 2205/3592* (2013.01); *A61M 2205/52* (2013.01)

(58) Field of Classification Search
CPC .......... A61M 2205/3584; A61M 16/16; A61M 2016/0027; A61M 2205/3561; A61M 2205/52; A61M 2205/3553; A61M 2016/0039; A61M 2205/3592; H04L 41/0803
See application file for complete search history.

(56) References Cited

U.S. PATENT DOCUMENTS

| | | | | |
|---|---|---|---|---|
| 2003/0093301 | A1* | 5/2003 | Chesney | G06F 19/328 705/3 |
| 2003/0105389 | A1* | 6/2003 | Noonan | G06F 19/3418 600/300 |
| 2003/0200116 | A1* | 10/2003 | Forrester | G06F 19/321 705/2 |
| 2004/0244807 | A1 | 12/2004 | Sun et al. | |
| 2004/0249250 | A1* | 12/2004 | McGee | A61B 5/0002 600/300 |
| 2005/0113650 | A1* | 5/2005 | Pacione | A61B 5/411 600/300 |
| 2006/0100905 | A1* | 5/2006 | Christen | G06F 19/328 705/2 |
| 2006/0218549 | A1* | 9/2006 | Hsu | G06F 8/65 717/174 |
| 2008/0046292 | A1* | 2/2008 | Myers | G06F 17/30557 705/3 |
| 2008/0097909 | A1 | 4/2008 | Dicks et al. | |
| 2009/0112630 | A1* | 4/2009 | Collins, Jr. | G06F 19/327 705/3 |
| 2019/0156924 | A1* | 5/2019 | Lewis | G16H 20/30 |

OTHER PUBLICATIONS

International Search Report; PCT/NZ2012/000106; dated Aug. 28, 2012.
Written Opinion; PCT/NZ2012/000106; dated Aug. 28, 2012.
Search Report in corresponding French Patent Application No. 1256116, dated Mar. 30, 2016, in 6 pages.
Office Action in corresponding European Patent Application No. 12804499.7, dated Jun. 12, 2019, in 9 pages.

* cited by examiner

DATA CAPTURE AND ROUTING SYSTEM AND METHOD

INCORPORATION BY REFERENCE TO ANY PRIORITY APPLICATIONS

Any and all application for which a foreign or domestic priority claim is identified in the Application Data Sheet as filed with the present application are hereby incorporated by reference under 37 C.F.R. § 1.57.

FIELD

The present disclosure relates to a system and method for capturing compliance data from a breathing apparatus and routing that data to a destination for further use.

BACKGROUND

Breathing assistance apparatus are used for a variety of purposes, including PAP, oxygen treatment and the like. When using such apparatus to treat a condition, it is important that the patient complies with the treatment prescription provided by their healthcare professional. If they do not comply with the treatment prescription (such as not using the apparatus in accordance with the healthcare professionals direction) then the treatment may not be successful. Compliance of the patient to their prescription is of interest to insurance providers who fund the apparatus and treatment, and also the dealers who provide the apparatus to patients.

Breathing apparatus can record compliance data for analysis so that patient compliance can be monitored and actions taken if necessary. The compliance data is normally obtained from sensors and other processors in the apparatus itself. The data is then provided to the healthcare professional, dealer, insurance provider or other interested party for review. The provision of compliance data requires some action from the patient themselves. Many patients have difficulties in ensuring they take the required actions to transmit the compliance data. This is due to a number of factors, including inability to use the technology, lack of awareness, forgetfulness, and/or lack of interest.

SUMMARY

It is an object of the present disclosure to provide a system that assists the provision of data from a breathing apparatus to an interested party for review.

In one aspect the present invention may be said to consist in a computer system for routing breathing apparatus usage data to a target recipient system of a plurality of recipient systems comprising: a processor and network interface configured to: receive input data comprising breathing apparatus usage data via a network, format the usage data into a destination format in accordance with formatting data, and routing the formatted usage data via a network to the target recipient system using routing information.

In another aspect the present invention may be said to consist in a method of routing breathing apparatus usage data to a target recipient system of a plurality of recipient systems comprising: receiving input data comprising breathing apparatus usage data via a network, formatting the breathing apparatus usage data into a destination format using formatting information, and routing the formatted usage data via a network to the target computer system using routing information.

In another aspect the present invention may be said to consist in a computer system for routing breathing apparatus usage data comprising: a processor and network interface configured to: receive input data comprising breathing apparatus usage data via a network, format the usage data into a destination format in accordance with formatting data, and transmit the formatted usage data via a network to a recipient system in accordance with routing information.

Preferably the recipient system is a target recipient system of a plurality of recipient systems and the routing information enables routing of the transmitted formatted data via the network to the target recipient system.

Preferably the input data further comprises the routing information and/or formatting information.

Preferably the input data is received directly or indirectly from the breathing apparatus via one or more of:
 GSM transmission from the breathing apparatus to the computer system,
 Mobile/landline telephone transmission from the breathing apparatus to a PC or to the computer system,
 VOIP transmission, using e.g. a VOIP handset to a PC or to the computer system
 Analogue or digital telephone modem from the breathing apparatus to a PC or to the computer system,
 WIFI transmission from the breathing apparatus to a PC or over a network to the computer system,
 Ethernet transmission from the breathing apparatus to a PC or over a network to the computer system,
 Removable memory device to transfer data between the breathing apparatus and a PC,
 Removable memory device to transfer data between the breathing apparatus to a kiosk connected to the computer system or a recipient system,
 Manual input of data displayed on the breathing apparatus into a PC or website,
 Manual/voice input of data displayed on the breathing apparatus into a mobile, landline or VOIP telephone to a PC or the computer system,
 Bluetooth™/Zigbee™ transmission from the breathing apparatus using a home hub or other network connected device to a PC or the computer system,
 Bluetooth transmission from the breathing apparatus to a mobile telecommunication device to a PC or the computer system.
 Data in audible form output from a speaker in the breathing apparatus over a mobile, landline or VOIP handset/telecommunications device to a PC or the computer system.

Preferably the routing information takes the form of one or more of:
 client ID based routing rules,
 device based routing rules,
 default routing rules.

Preferably the data originates from one of a plurality of breathing apparatus.

Preferably the usage data is compliance data.

Preferably each recipient system is operated by or on behalf of a service provider and/or an interested party being one or more of a:
 insurance company,
 medical equipment dealer,
 healthcare professional, and/or
 patient Preferably each recipient computer system comprises one or more of a database, reporting tool and/or user terminal being operated by or on behalf of a service provider and/or one or more interested parties.

In another aspect the present invention may be said to consist in a method of routing breathing apparatus usage data comprising: receiving input data comprising breathing apparatus usage data via a network, formatting the breathing apparatus usage data into a destination format using formatting information, and transmitting the formatted usage data via a network to a recipient system in accordance with routing information.

Preferably the recipient system is a target recipient system of a plurality of recipient systems and the routing information enables routing of the transmitted formatted data via the network to the target recipient system.

Preferably the input data further comprises the routing information and/or formatting information.

Preferably the input data is received directly or indirectly from the breathing apparatus via one or more of:
- GSM transmission from the breathing apparatus to the computer system,
- Mobile/landline telephone transmission from the breathing apparatus to a PC or to the computer system,
- VOIP transmission, using e.g. a VOIP handset to a PC or to the computer system
- Analogue or digital telephone modem from the breathing apparatus to a PC or to the computer system,
- WIFI transmission from the breathing apparatus to a PC or over a network to the computer system,
- Ethernet transmission from the breathing apparatus to a PC or over a network to the computer system,
- Removable memory device to transfer data between the breathing apparatus and a PC,
- Removable memory device to transfer data between the breathing apparatus to a kiosk connected to the computer system or a recipient system,
- Manual input of data displayed on the breathing apparatus into a PC or website,
- Manual/voice input of data displayed on the breathing apparatus into a mobile, landline or VOIP telephone to a PC or the computer system,
- Bluetooth™/Zigbee™ transmission from the breathing apparatus using a home hub or other networked device to a PC or the computer system,
- Bluetooth transmission from the breathing apparatus to a mobile telecommunication device to a PC or the computer system.
- Data in audible form output from a speaker in the breathing apparatus over a mobile, landline or VOIP handset/telecommunications device to a PC or the computer system.

Preferably the routing information takes the form of one or more of:
- client ID based routing rules,
- device based routing rules,
- default routing rules.

Preferably the data originates from one of a plurality of breathing apparatus.

Preferably the usage data is compliance data.

Preferably each recipient system is operated by or on behalf of a service provider and/or an interested party being one or more of a:
- insurance company,
- medical equipment dealer,
- healthcare professional, and/or
- patient Preferably each recipient system comprises one or more of a database, reporting tool and/or user terminal being operated by or on behalf of a service provider and/or one or more interested parties.

In another aspect the present invention may be said to consist in a breathing apparatus usage data capture system at least one user computer comprising: a device interface for receiving a memory device containing usage data, a processor configured to automatically execute an application that retrieves usage data from a memory device via the interface when the memory device is connected to the device interface, and a network interface to transmit the usage data across a network, and a computer system comprising a network interface and processor configured to: receive data from and/or transmit data to the user computer via a network, and transmit data to the user computer to communicate a reminder for the user to connect the memory device to the device interface.

Preferably the application is stored on the memory device.

Preferably the application is downloaded from a webserver and is executed upon the user accessing a website provided by the webserver.

Preferably the memory device is a portable device such as a USB memory device.

Preferably the reminder is communicated by way of:
- telephone
- facsimile
- email/instant messaging
- text message
- the internet
- user IO on the breathing apparatus.

In another aspect the present invention may be said to consist in a method of routing breathing apparatus usage data: providing an application that automatically executes on a user computer to retrieve usage data from a memory device via the interface when the memory device is connected to the device interface, and transmits the usage data across a network, and providing a computer system comprising a network interface and processor configured to: receive data from and/or transmit data to the user computer via a network, and transmit data to the user computer to communicate a reminder for the user to connect the memory device to the device interface.

Preferably the application is stored on the memory device.

Preferably the application is downloaded from a webserver and is executed upon the user accessing a website provided by the webserver.

Preferably the memory device is a portable device such as a USB memory device.

In another aspect the present invention may be said to consist in a method of capturing usage data comprising: receiving a memory device containing usage data at device interface of a user computer, automatically executing an application on the user computer that retrieves usage data from the memory device transmitting the usage data to a computer system, and transmitting data from the computer system to the user computer to communicate a reminder for the user to connect the memory device to the device interface.

Preferably the application is stored on the memory device.

Preferably the application is downloaded from a web server and is executed upon the user accessing a website provided by the web server.

Preferably the memory device is a portable device such as a USB memory device.

Preferably the reminder is generated based on the time elapsed since the last usage data upload.

Preferably the reminder is communicated by way of:
- telephone
- facsimile email/instant messaging
text message
the internet
user IO on the breathing apparatus.

In another aspect the present invention may be said to consist in a computer system for routing breathing apparatus compliance data comprising: a processor and network interface configured to: receive input data comprising breathing apparatus compliance data via a network, format the compliance data into a destination format in accordance with formatting data, and transmit the formatted compliance data via a network to a recipient system in accordance with routing information.

In another aspect the present invention may be said to consist in a method of routing breathing apparatus compliance data comprising: receiving input data comprising breathing apparatus usage data via a network, formatting the breathing apparatus compliance data into a destination format using formatting information, and transmitting the formatted compliance data via a network to a recipient computer system in accordance with routing information.

In another aspect the present invention may be said to consist in a breathing apparatus compliance data capture system at least one user computer comprising: a device interface for receiving a memory device containing compliance data, a processor configured to automatically execute an application that retrieves compliance data from a memory device via the interface when the memory device is connected to the device interface, and a network interface to transmit the compliance data across a network, and a computer system comprising a network interface and processor configured to: receive data from and/or transmit data to the user computer via a network, and transmit data to the user computer to communicate a reminder for the user to connect the memory device to the device interface.

Preferably the application is stored on the memory device.

Preferably the application is downloaded from a webserver and is executed upon the user accessing a website provided by the webserver.

Preferably the memory device is a portable device such as a USB memory device.

In another aspect the present invention may be said to consist in a method of routing breathing apparatus compliance data: providing an application that automatically executes on a user computer to retrieve compliance data from a memory device via the interface when the memory device is connected to the device interface, and transmits the compliance data across a network, and providing a computer system comprising a network interface and processor configured to: receive data from and/or transmit data to the user computer via a network, and transmit data to the user computer to communicate a reminder for the user to connect the memory device to the device interface.

Preferably the application is stored on the memory device.

Preferably the application is downloaded from a webserver and is executed upon the user accessing a website provided by the webserver.

Preferably the memory device is a portable device such as a USB memory device.

In another aspect the present invention may be said to consist in a method of capturing compliance data comprising: receiving a memory device containing compliance data at device interface of a user computer, automatically executing an application on the user computer that retrieves compliance data from the memory device transmitting the compliance data to a computer system, and transmitting data from the computer system to the user computer to communicate a reminder for the user to connect the memory device to the device interface.

Preferably the application is stored on the memory device.

Preferably the application is downloaded from a web server and is executed upon the user accessing a website provided by the web server.

Preferably the memory device is a portable device such as a USB memory device.

Preferably the reminder is generated based on the time elapsed since the last compliance data upload.

Preferably the reminder is provided by way of:
telephone
facsimile
email/instant messaging
text message
the internet
user IO on the breathing apparatus.

In this specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Embodiments of the disclosure will be described with reference to the following drawings of which.

DETAILED DESCRIPTION

Overview of System

Figure 1:
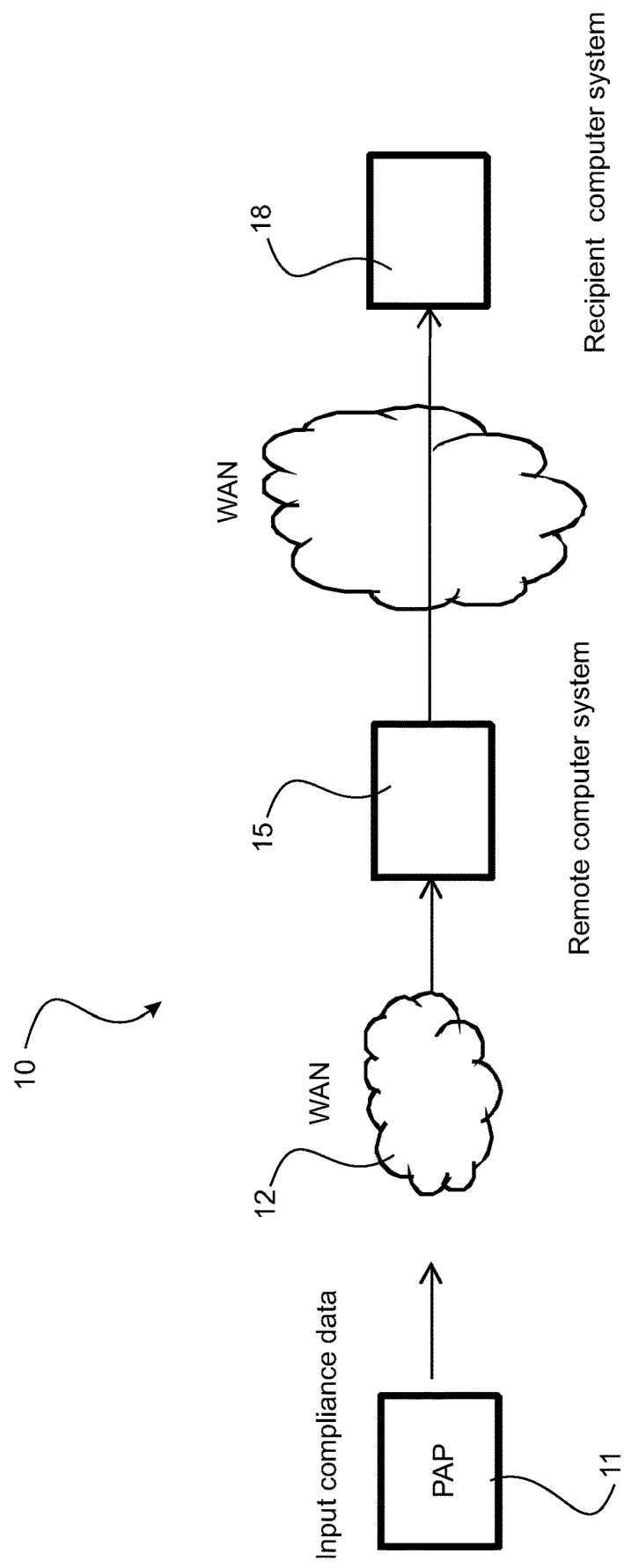
FIG. 1 shows an overview of a system for obtaining and forwarding breathing apparatus compliance data.

FIG. 1 shows a system 10 that provides for compliance data transfer. Embodiments of the present invention form at least part of the system. Briefly, the system provides for the transfer of information comprising usage/therapy data (such as compliance and other efficacy and patient data that shown in table 1 below) and other data from a patient breathing apparatus 11, such as a CPAP apparatus, to a remote computer system 15 with routing functionality for reformatting and routing onto one or more recipient computer systems (also termed "destination computer systems") 18 for reporting and analysis purposes for interested parties (also termed "recipients" or alternatively "clients"). It will be appreciated that the term "compliance data" used through the specification could be extrapolated to cover any usage/therapy data (such as efficacy data) and mention in the embodiments described of "compliance data" should not be considered limiting.

Interested parties can be insurance companies, dealers and health professionals, for example. The information can be passed directly from the breathing apparatus 11 over a communications channel and WAN network 12 to the computer system 15, or it can be passed to a PC computer (shown in FIG. 2a) or other user apparatus for subsequent transfer over a WAN network to the computer system 15. The computer system 15 includes a router/router functionality that reformats and routes the information to the recipient computer system 18. A reminder server 150 (shown in FIG. 2a) is also provided, that provides reminders to a user via the PC and/or breathing apparatus to upload compliance data and other usage/therapy data. A service provider manages/facilitates and operates part or all of the system overall system 10.

The overall system and its operation will now be described in more detail with reference to FIG. 2a and the flow chart in FIG. 3. Each patient has a breathing apparatus at their residence 11. The remaining description will refer to the breathing apparatus as a CPAP apparatus by way of example—this should not be considered limiting. The apparatus could be any PAP or other breathing apparatus. The patient preferably will also have a computer 13, such as a PC, at their residence (or elsewhere if using e.g. GSM transmission) which is connected to a wide area network (WAN) 12, such as the internet, via a suitable connection. The CPAP apparatus 11 can be directly or indirectly in communication with the WAN 12 via a wireless or wired connection 21, 22. For example, it could be in communication with the WAN 12 via an wired or wireless external or internal modem 23, 24 or other interface using the standard telephone line or a mobile telecommunications network (such as GSM) 21, 22. In another alternative, the CPAP apparatus includes an external or internal transmission device 23, 24 for transmitting the information to the WAN 12 over a telecommunications network, such as a mobile telephone network 21, 22. Alternatively, another wireless communications system or network could be used to communicate with the WAN. This allows for transfer of the information from the CPAP machine over the WAN to the remote computer system 15 with router functionality.

Alternatively or additionally, the CPAP apparatus can be directly 25 or indirectly connected to the PC. This also allows for transfer of the information from the CPAP over the WAN 12 (via the PC) to the remote computer system 15. The CPAP apparatus can communicate with the PC via a wired or wireless communication channel 25. Alternatively, the patient can utilize a removable memory device 27 to transfer the information between the CPAP apparatus 11 and PC 13 by physically coupling the memory device to each apparatus 11, 13 to transfer data. The PC can then transfer the information over the WAN to the remote computer system 15, via any suitable communication network or system. The CPAP apparatus and/or PC can be arranged to receive reminders or triggers to transfer the data via a suitable medium, or to display those reminders to a patient to remind them to operate the CPAP machine to transfer the information. Alternatively, the user can receive such reminders via a telephone, mobile telephone or other communications device 28. In yet another alternative, the removable memory device 27 could be inserted into a kiosk 29 or similar, if the user is away from their home computer. The kiosk 29 is in communication with the remote computer system 15 via a telecommunications network/WAN.

In summary, any of the following modes can be used to transfer information from the CPAP apparatus 11 to the remote computer system 15.

GSM transmission from CPAP apparatus to remote computer system, e.g. 23 or 24, 21 or 22 or 25, Mobile/landline telephone transmission from CPAP apparatus to PC or to remote computer system e.g. 28.

VOIP transmission, using e.g. a VOIP handset e.g. 28.

Analogue or digital telephone modem from CPAP apparatus to PC or to remote computer system e.g. 23 or 24, 21 or 22 or 25.

WIFI (or other wireless) transmission from CPAP apparatus to PC or over network to remote computer system e.g. 23 or 24, 21 or 22 or 25.

Ethernet (or other wired) transmission from CPAP apparatus to PC or over network to remote computer system e.g. 25.

Removable memory device to transfer data between CPAP apparatus and patient PC e.g. 27.

Removable memory device to transfer data between CPAP apparatus to kiosk connected to remote computer system or recipient system e.g. 27, 29.

Manual input of data displayed on CPAP apparatus into a website.

Manual/voice input of data displayed on CPAP apparatus into a mobile, landline or VOIP telephone e.g. 28.

Bluetooth™/Zigbee™ transmission from CPAP apparatus using via a home hub or other network connected device.

Bluetooth transmission from CPAP apparatus to mobile telecommunication device.

Data in audible form from CPAP apparatus speaker over a mobile, landline or VOIP handset/telecommunications device to the PC or remote computer system.

These are just some examples of the transmissions methods, and it will be appreciated other transmission methods could be envisaged by those skilled in the art.

The remote computer system 15 is connected to the WAN 12. As previously noted, the computer system can receive data directly from the CPAP apparatus 11 over the WAN 12, or via the user PC 13. The remote computer system 15 includes router functionality and is operated by either a provider of the system, an agent of the provider or other third party. The information that the computer system 15 receives includes compliance and other data relating to usage of the CPAP apparatus 11 by the patient. The information might also comprise routing data indicating where the compliance data should be routed to, and formatting data specifying how the compliance data should be formatted for the recipient. Alternatively the routing and/or formatting data could be stored in the remote computer system 15, or received via another source.

The computer system 15 uses the routing and formatting data to reformat the compliance data and route it to an appropriate recipient computer system or systems (shown generally as 18 in FIGS. 1 and 2a) for providing the reporting/analysis services to interested parties (e.g. insurance companies, dealer, healthcare professionals and/or patient). The recipient computer system 18 usually takes the form of multiple recipient computer systems e.g. 18a-18d, each for storing and reporting clinical information for different interested parties. Each recipient computer system e.g. 18a-18d (hereinafter: simply referred to as the recipient computer system 18) includes a database that stores the reformatted and routed compliance data and other information, and a server that provides reporting services/tools for presenting the reports and information to the interested parties (e.g. dealer, healthcare professional, insurance provider, and/or patient.) The server and database for each can be located remotely from each other or in the same location. Reporting services/tools comprise software tools for presenting reports and information on clinical information in relation to a patient to the interested parties. The reporting tools/services can be accessed by individuals in an interested party through a PC connected to the report server via a network. This enables those interested parties to review and understand information pertaining to each patient and their use of the CPAP machine.

Each recipient computer system 18 might be operated by the interested parties or a third party or the system provider. Each recipient computer system is for a different interested party. Each recipient computer system 18 can be configured/operated in various ways, depending on the requirements of the interested parties, examples of different configurations are labelled 18a-18d in FIG. 2a. A party might fully or partially operate the recipient computer system themselves, or commission a third party to fully or partially operate the recipient system on their behalf. A number of different configurations/options are possible. Some parties want to retain full control of the information and reporting services. Others will allow the information to be stored and controlled by another party and/or allow the reporting services to be provided by another party, such as the service provider. Any one or more of the configurations could form part of the overall system, each recipient computer system configuration being for use by one of the many interested parties that will use the overall system.

In one embodiment, the recipient computer system 18 is a server 19a operated by or on behalf of the service provider for providing reporting services to the interested party 18a. In this embodiment, the database e.g. 203 resides with the server 19a (as shown in FIG. 2a, or is remote but in communication with the server 19a). The server 19a with database 203 is shown in more detail in FIG. 2b. The server 19a provides report tools (e.g. the user interface (UI) viewer 19b). The server 19a comprises a network interface 200 for receiving information routed from the remote computer system 15. The information is passed to an input data processor 201 and on to a server controller 202. The server controller 202 manages the data domain, processes commands and requests with respect to the data domain. Command and query handlers 204 provide reporting tools for reporting the output via the network interface 200. The server 19a comprises or is in remote communication with the database 203 that stores the relevant information (that is, the reformatted routed compliance data and other information) for the interested parties and is passed to the server that provides the reporting tools 19b. In one variation, the server provides a client/server software solution reporting tool 19b that resides on the server 19a (or elsewhere) and on the interested party's computers (e.g.

PC/desktop computer 19c). The interested party (which comprises individuals from the interested party) can access the information via a software reporting tool on their computer 19c (which has a Graphical User Interface (GUI)), which obtains the information from the server 19a, over a WAN such as the internet. In another variation, the server 19a is a web server that provides web-based reporting tools. The interested party can access the information via a browser on their computer 19c, which obtains the information from the web server over the internet. In this embodiment, the service provider provides the reporting client/viewer 19b.

In yet a further variation 18c a third party can access the database 203 and server 19a, but provide their own reporting user interfaces and tools (UI report viewer or report client) 19b. Interested parties can access relevant information on their PC 19c (through a GUI) via the third party user interfaces/reporting tools 19b, rather than using those provided by the service provider as was indicated in the example of the server 19a. In yet a further alternative 18c, the interested party provides their own reporting user interfaces and tools (UI report viewer or report client) 19b. Interested parties can access relevant information using their user interfaces, rather than using those provided by the service provider.

In another embodiment 18d, the recipient computer system is a server operated by or on behalf of interested party for providing reporting services to the interested party. In this embodiment, the database resides along with the server 19d. The database is the same or similar to the database 203 previously shown and described with respect to FIG. 2a. The server 19d comprises (or remotely communicates with) the database that stores the relevant information (that is, the reformatted routed compliance data and other information) for the interested parties and is passed to the server 19a that provides the reporting tools 19b. The interested party provides their own reporting user interfaces and tools (report viewer or report client) 19b. Interested parties can access relevant information using their user interfaces 19b using PCS 19c with GUIs, rather than using those provided by the service provider. In a variation, the service provider provides the reporting client/viewer.

In another embodiment, the recipient computer system 18b is a server 19a operated by or on behalf of the service provider. However, using an API 19e, the interested party can retrieve the information into a local system 18b (such as an electronic medical record (EMR)/patient management system database 19f) for use and reporting via that system through a PC 19c and GUI. Integration into an online EMR could also occur. The local system 18b is operated by or on behalf of the interested party.

Various other configures/architectures of recipient computer systems could also be envisaged and the invention is not limited to those described above.

The various embodiments of recipient computer systems 18a-18d allow for the following:

the service provider to host all data and provide all reporting, the interested party to host all data and provide all reporting, or a mix between the service provider hosting data/providing reporting and the interested party hosting data/providing reporting.

The system 10 also has a reminder server 150 that generates and provides for reminders so that a patient is prompted to operate their computer and/or CPAP apparatus 11 to transfer data comprising compliance data to the remote computer system/router 15. This could be hosted by any suitable party and for exemplary purposes is shown coupled to the database hosted by the service provider.

Figure 2A:
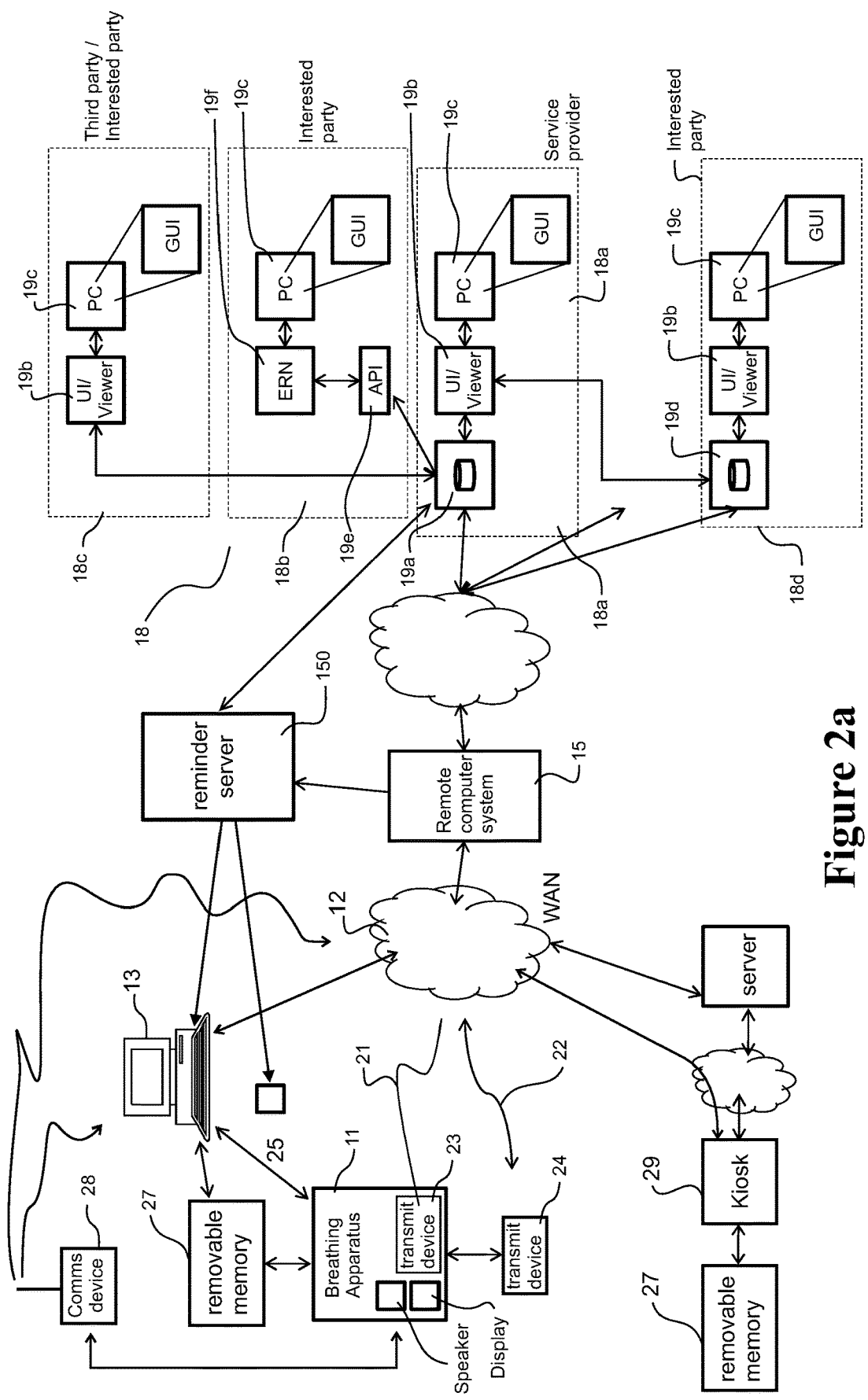
FIG. 2a shows the system in more detail.
Figure 2B:
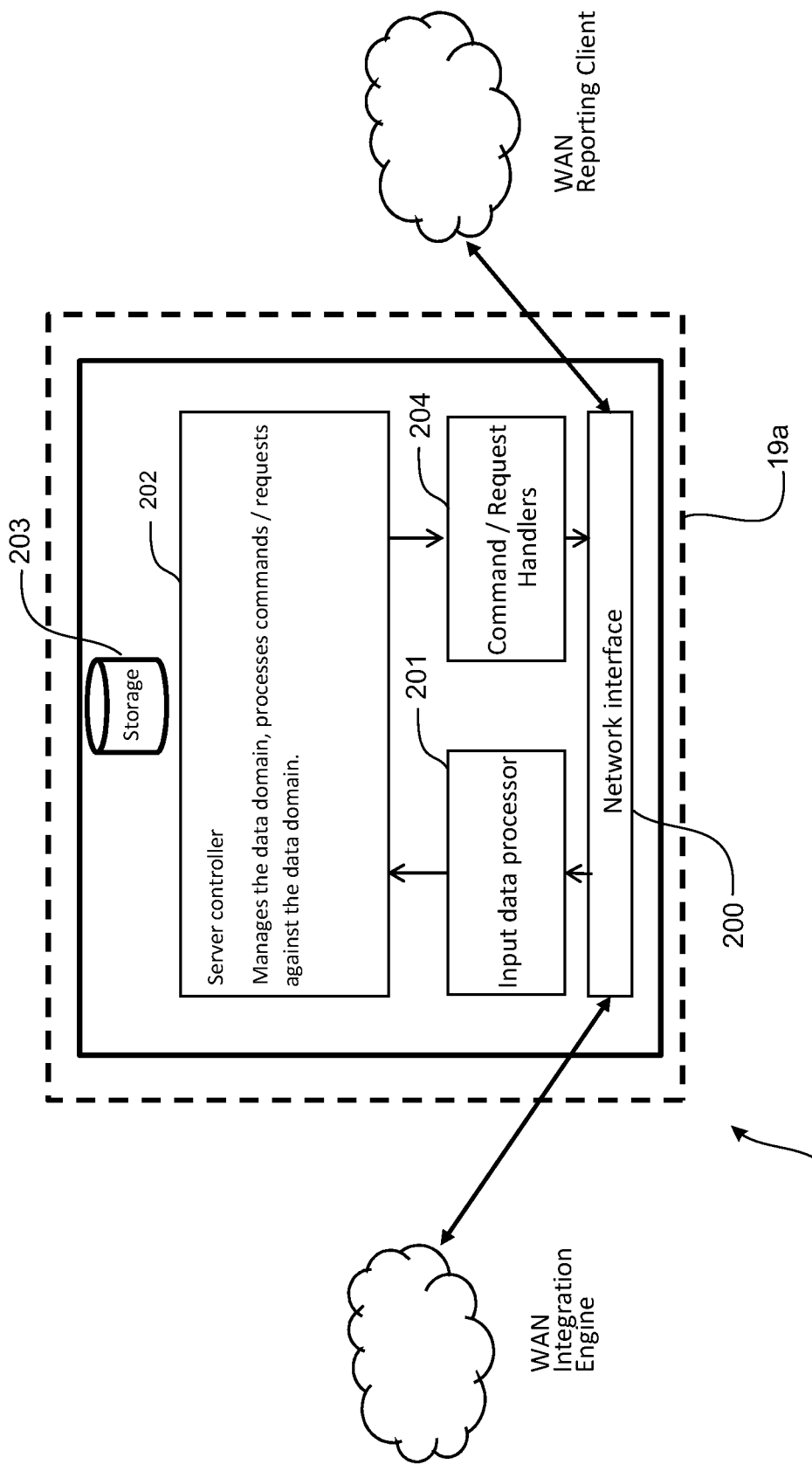
FIG. 2b shows the reporting server in more detail.

FIGS. 1 and 2 show only one PC and CPAP apparatus, however it will be appreciated that the system is arranged to receive data, including compliance and other usage/therapy data from a plurality of patient CPAP machines in various locations, and reformat and route that data to the appropriate database/server (recipient computer system) for providing reporting services (either operated by or on behalf of the interested party or the provider) for a range of interested parties. It will also be appreciated that the various embodiments do not necessarily need to comprise every component shown in FIGS. 1 and 2a. FIGS. 1 and 2a show possible options, of which some or all might be present. Some components of the system such as the breathing apparatus, user computer and third party computer systems can be considered optional for connection to the system, but not an integral part thereof.

The operation of the system will be briefly described with reference to FIG. 3. A reminder to upload data to the computer system can optionally be sent to the user, step 40. Upon reminding, or of their own accord, the user can effect upload of compliance and other usage/therapy data to the remote computer system 15 via any one of the modes described above. Alternatively, the CPAP apparatus and/or PC automatically upload the compliance data. The compliance data is received by the computer system, step 41. The computer system 15 reformats and routes the compliance data to the recipient's computer system 18, based on reformatting and routing data, step 42. The compliance data is stored on the recipient computer system database, step 43, then transferred to the recipient's reporting server (which may encompass the database), step 44. The recipient report server then provides reporting services to the recipient, step 45.

Detailed Description of Components and Operations of the System

Figure 4:
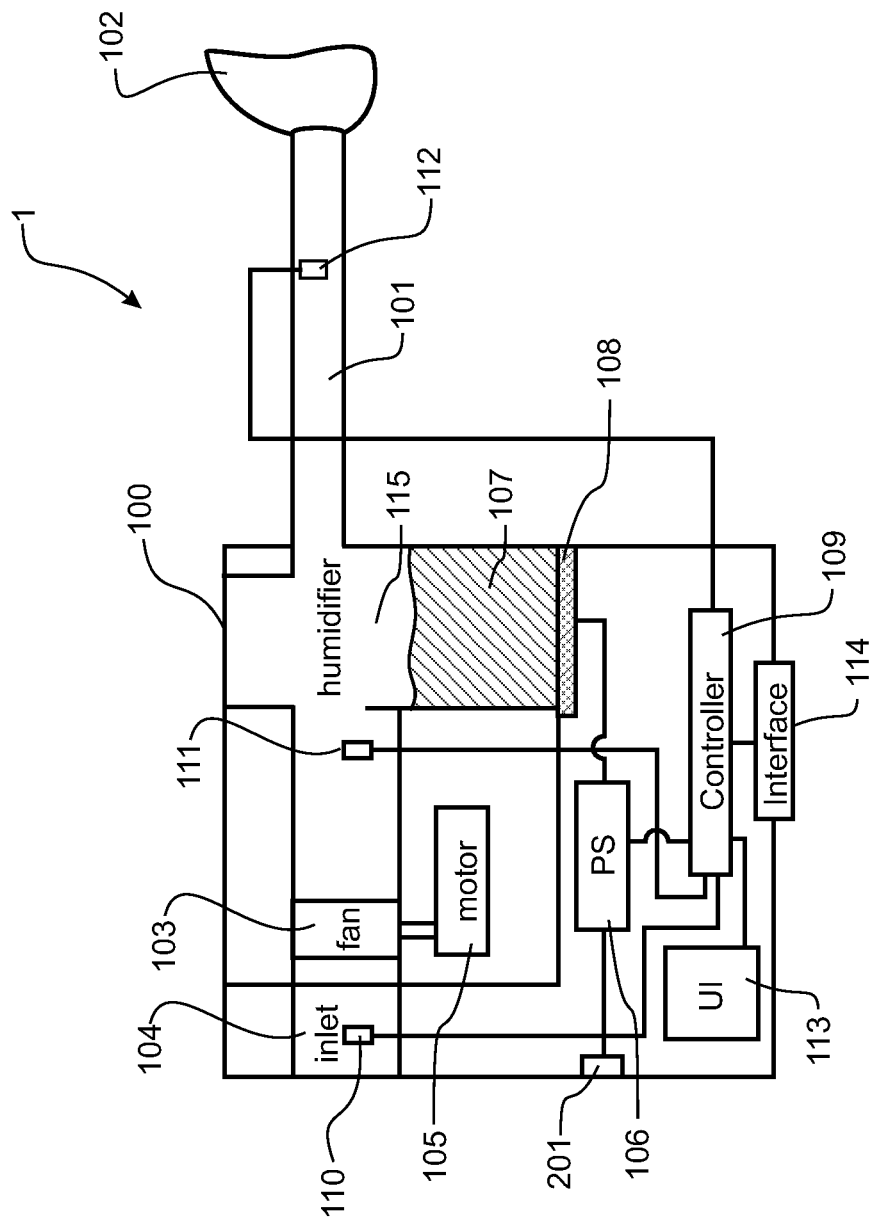
FIG. 4 shows a CPAP breathing apparatus.

The configuration and operation of aspects of the system will now be described in further detail Breathing Apparatus FIG. 4 is a block diagram illustrating one embodiment of a breathing gases supply system 1 that might be used in the system of FIG. 1. The full system includes a PAP apparatus 100 for delivering a supply of breathing gases, a breathing circuit 101 and a patient interface 102.

The supply conduit 101 extends from an outlet in the PAP apparatus 100 and to the patient interface 102. The patient interface may be any suitable sealing patient interface such as a full face mask, nasal mask, nasal pillows, oro-nasal mask, oral mask, oral interface, nasal seal, nasal cannula and so on.

The PAP apparatus 100 includes a blower. The blower preferably includes a fan 103 driven by an electric motor 105. Air is drawn into the PAP apparatus 100 through the inlet 104 by the fan 103. Pressurised air leaves the fan 103 for supply to the patient. Alternatively, controllable flow generators may draw on a source of high pressure gas, and regulate a flow of gas from the high pressure source.

The PAP apparatus 100 preferably includes a humidifier 115 in the embodiment of FIG. 1. In alternative embodiments the humidifier 115 may be separate from the PAP apparatus and part of the breathing gases supply system 1 or alternatively there may be no humidifier 115 present. The humidifier 115 as shown in FIG. 1 is a pass over type humidifier where air passing through the humidifier picks up a quantity of water vapour from a reservoir of water 107. The water reservoir 107 may be heater by a heater 108. The humidifier 115 is preferably integrated into the housing of the PAP apparatus 100. Alternatively the humidifier 115 may be a separate component within the housing of the PAP apparatus or separate from the PAP apparatus 100 with a conduit connecting between the PAP apparatus 100 and the humidifier 115. Other types of humidifiers, other than a pass over type may be used. In some forms or embodiments multiple humidifiers may used in the breathing gases supply system 1.

The heater 108 and the motor 105 are supplied by a power supply (PS) 106. The amount of power supplied to the motor determines the speed the fan 103 turns at. The amount of power supplied to the heater 108 determines the amount of water vapour produced by the humidifier 115 and hence is one way of controlling the amount of humidification of the breathing gases supplied by the PAP apparatus 100. The amount of power supplied by the power supply 106 is controlled by the outputs of a controller.

The PAP apparatus preferably includes a first controller 109. The first controller 109 preferably is used to control the blower and breathing circuit. The controller 109 is supplied by power from the power supply 106. The controller receives inputs from a user interface (UI) 113. The user interface could be in the form of any suitable user interface such as a knob, a plurality of buttons, a screen or any combination thereof. The user interface 113 allows the PAP apparatus 100 to display information to the user and also allows a user to input information to the PAP apparatus, more particularly to the controller 109. The controller 109 may also be provided with an interface 114 for connecting to an external data source. The external data source may for example, be a communication interface such as a modem, or may be an interface to an external memory such as a smart card, USB, flash drive, disk drive or the like. The interface is capable of connection with a mobile storage device. For generic use, the interface 114 may be a data communications port according to any available standards for example a universal serial bus (USB) port. The interface 114 may also be capable of wireless communications such as Bluetooth, infrared and the like. The interface 114 may also be capable for connecting to a wide range of peripheral devices.

The controller 109 typically includes an embedded microcomputer with stored control programs for controlling various aspects of the PAP apparatus 100 and operation of these aspects. Alternatively the controller 109 may be removable from the PAP apparatus 100. In a further alternative form the controller 109 may be remote to the PAP apparatus 100.

The controller 109 preferably includes interfaces for receiving inputs from a user interface 113 and for receiving inputs from one or more sensors which preferably comprise a flow sensor 110, a pressure sensor 111 downstream to the fan and a flow sensor 112 that is placed close to or on the patient interface to determine the flow or velocity of gases supplied to the patient or user. The flow sensor 110 may be positioned upstream or downstream to the fan 103. The sensors are one configuration of sensors that can be used in the breathing gases supply system 1. Any other configuration of sensors and any other types of sensors may be used. There may be fewer or more sensors than those shown. There may a variety of other sensors that measure other data such as humidity sensors, mass flow sensors, temperature sensors and the like.

In the embodiment shown, the breathing gases supply system 1 includes at least a flow sensor 110 and pressure sensor 111 in the PAP apparatus 100 and a flow sensor 112 adjacent the patient interface 102. The data measured by the sensors, i.e. flow and pressure, will be referred to as breathing data because it signifies data that relates to the breathing of the patient. The two common variables measured are pressure and flow of gases breathed or supplied to the patient or user.

The apparatus also includes an interface for receiving a removable memory device (such as a USB storage device). The interface is coupled to the processor such that information can be uploaded to the processor from the removable memory device, and downloaded to the removable memory device from the processor.

Figure 5:
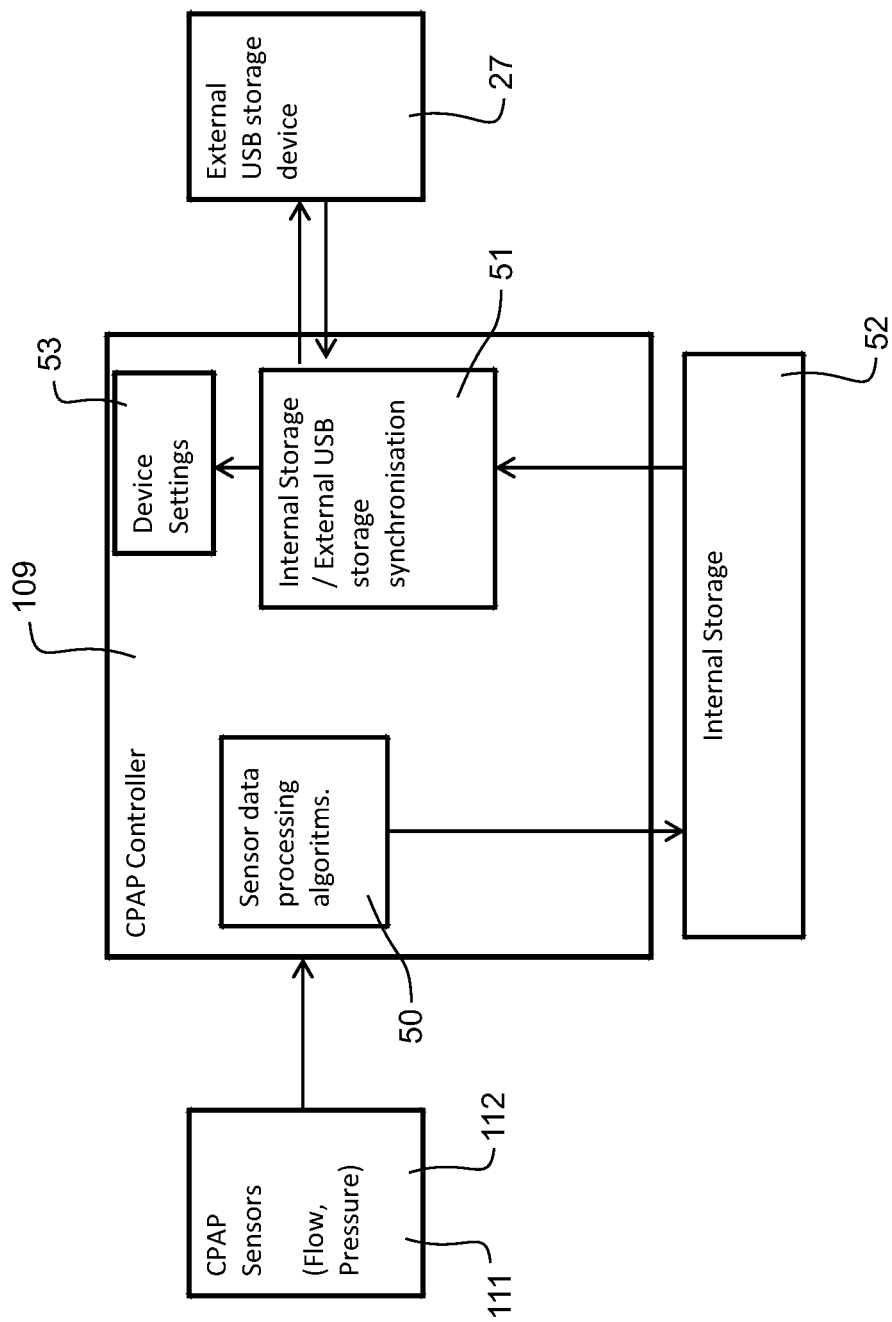
FIG. 5 shows the controller in more detail.

FIG. 5 shows the controller and sensors in more detail. Parameters are measured by flow, pressure and any other suitable sensors 111, 112 attached to the CPAP apparatus 11 and the information is passed as data/signals to the controller 109. The information can be processed by algorithms 50 in the controller that determine compliance and efficacy information from these signals, as known by those skilled in the art, and stored in internal storage 52. Some or all of the following information is derived: flow, mask leaks, min/max pressures, average pressures, $90^{th}$ percentile pressures, AI, HI, awakenings, apnea events, hypopnea events, flow limitation events. This information is stored as data in the breathing apparatus internal memory for each usage session. Two types of data are stored, summary and detailed data, each in a different data table.

An example summary usage data is shown in the table below that includes usage time, compliance time (compliance data), AI, HI, $90^{th}$ percentile pressure, average pressure, $90^{th}$ percentile leak, average leak and awakenings for a usage session (efficacy data), one of these table entries is created each usage session.

When a usage session ends or a removable memory device is connected to the breathing apparatus, the controller 109 will synchronise any internally stored data, not yet on the memory device, to the removable memory device. To do this, the controller has an internal storage/external USB storage synchronisation function/area 51 which stores a last session synchronised marker internally, and compares this marker to the latest session logged. If there is summary usage session data to be synchronised in the internal summary table, these entries are copied by the controller, to a summary file on the memory device. If no summary file exists, one is created by the controller. If there is detailed usage data to be synchronised in the internal detailed data table, these entries are copied by the controller, to a detailed file on the USB storage device. If no detailed file exists one is created by the controller. The files are created with a fixed size and when one fills up, another is created. The files exist within a FAT32 file system on the USB storage device. Synchronisation occurs as set out by device settings 53.

In order to correlate detailed data table entries to a usage session an index table exists that stores the session date, time and the first row of data in the detailed table for that session and the number of rows of data in the detailed table that are included in that session. An entry is created every usage session. An example of an entry is shown in the table below.

TABLE 1

| Session Date/Time | usage time (hh:mm) | Compliance time | AI | HI | $90^{th}$ percenttile pressure | average pressure | $90^{th}$ percentile leak | average leak | awakenings |
|---|---|---|---|---|---|---|---|---|---|
| Session #1 Jan. 1, 2011 10:54:00 | 5:50 | 4:15 | 5 | 7 | 12.0 | 10.0 | 40 | 30 | 5 |

An example of detailed usage data is shown below that includes, leak, pressure, apnea events, hypopnea events, flow limitation events and awakenings, one of these entries is created every two minutes within a usage session.

TABLE 2

| Sample | Pressure | Leak | Apnea event | Hypopnea Event | Flow limitation event | A-wakening |
|---|---|---|---|---|---|---|
| 2 minutes | 10 | 43 | 1 | 0 | 0 | 0 |
|  |  |  | 1 | 0 | 0 | 0 |
|  |  |  | 0 | 0 | 0 | 0 |
|  |  |  | 0 | 0 | 0 | 0 |
|  |  |  | 0 | 0 | 0 | 0 |
|  |  |  | 0 | 0 | 0 | 1 |
| 4 minutes | 10.2 | 44 |  |  |  |  |
| 6 minutes | 10.1 | 43 |  |  |  |  |
| 8 minutes | 10.2 | 42 |  |  |  |  |

TABLE 3

| Date/Time | Detailed Table row start index | Rows in session |
|---|---|---|
| Jan. 1, 2011 10:54:00 | 1 | 100 |
| Jan. 2, 2011 11:23:00 | 101 | 43 |

A detailed file on the removable memory device contains a header describing the file type, device serial number and device model, the *index* table, followed by the detailed data table.

After download, the removable memory device holds the information in the detailed and the summary tables. This includes compliance data, which is broadly used to mean any information relating to compliance, or form which compliance can be determined. Other information can be stored also—such as efficacy data or other usage/therapy data. References to compliance data will be used to cover any type of information relating to operation of the breathing apparatus.

Data Transmitting Components and Operation

Figure 3:
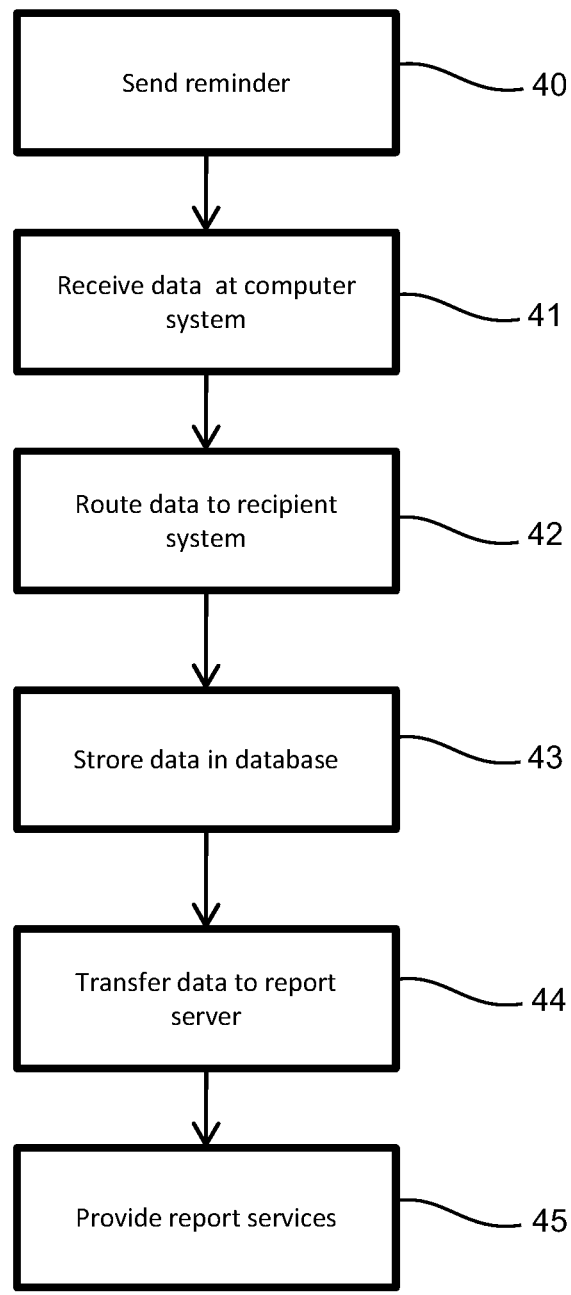
FIG. 3 shows a flow chart of the operation of the system.

Periodically or in an ad hoc manner, and either automatically or upon action by the patient, either with or without a reminder, information that includes the compliance data that the CPAP apparatus has obtained is transferred across the WAN and received by the remote computer system 15, step 41 in FIG. 3. Where transfer is made upon action by the patient, this might be in response to a reminder provided by the system, in a manner to be described later. Optionally, routing data and formatting data is also transferred to the remote computer system 15 from the CPAP apparatus (although this might already exist on the remote computer system 15). The information is transferred in one of several ways. In any of these alternatives, where user intervention is required, the user can receive a reminder to take action to ensure transfer of the information occurs. The reminder system will be discussed in detail later.

Figure 6:
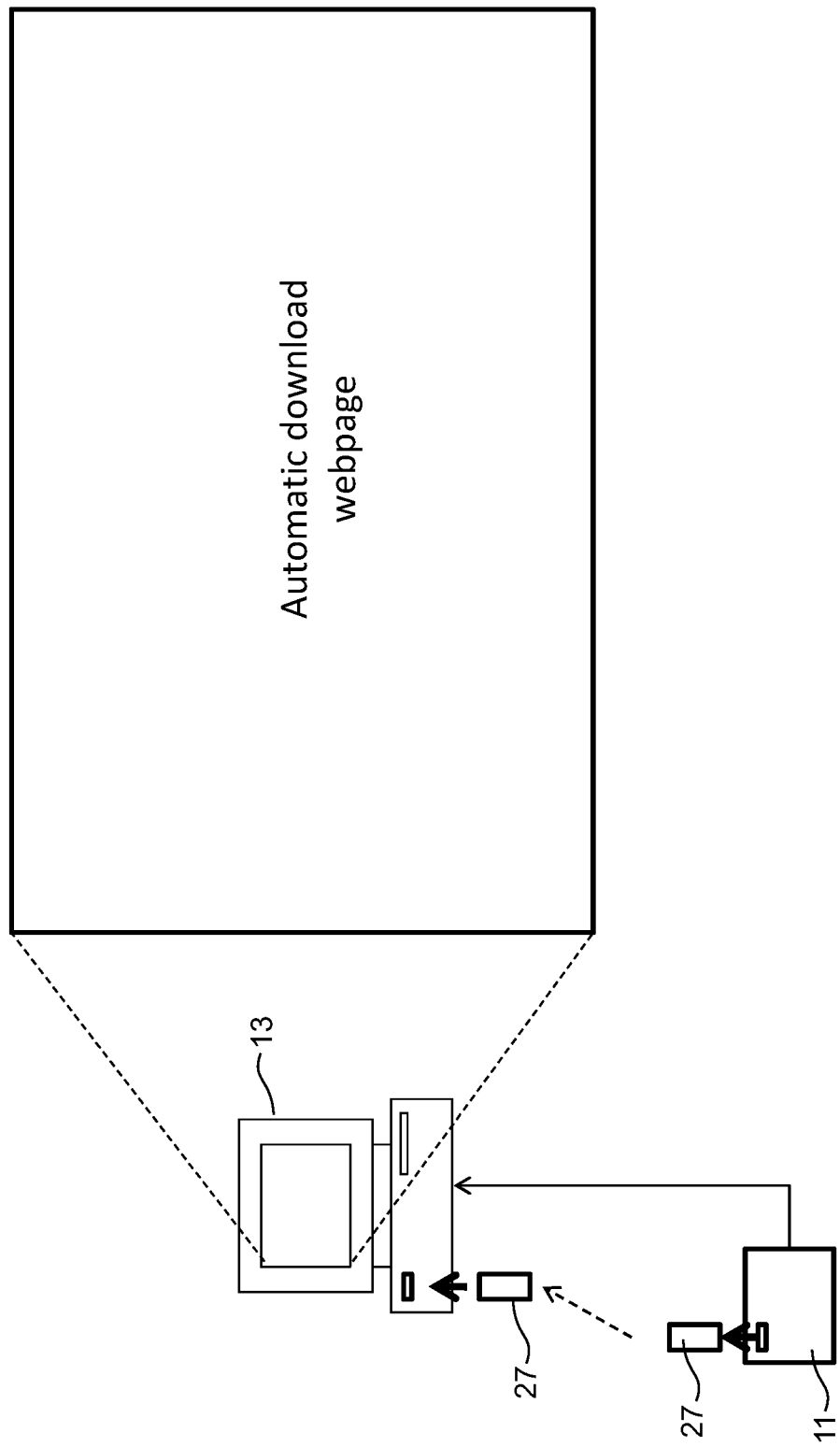
FIG. 6 shows a user computer displaying a browser and auto-executed application.

Referring to FIG. 6, various alternatives of data transfer are described. In a first alternative the CPAP apparatus 11 includes or is connected to an internal or external modem or other interface that connects the CPAP apparatus wirelessly or wired to the WAN. In another alternative, the CPAP apparatus includes an external or internal transmission device for transmitting the information to the WAN over a telecommunications network, such as a mobile telephone network. In another alternative, the CPAP apparatus can be connected to the PC, either wirelessly or through a suitable connection, to transfer the data to the centralised computer system via the PC. In another alternative the CPAP apparatus can be directly connected to the WAN through a patient home connection such as WIFI™, Ethernet™ or Zigbee™. Yet further alternatives are possible, as previously mentioned.

In any of the above communication alternatives, download of the compliance data from the CPAP machine across the WAN to the computer system 15 can be triggered by user action (such as activating a control) or automatically by the CPAP machine. For example, in one variation, when a treatment session ends or at a scheduled time the modem or other transmission interface is signalled, and initiates a download of the compliance data from any previous sessions to the computer system 15 and also stores this information internally. The modem or other interface may also receive a settings update from the computer system 15 at that time and is able to apply this update to the modem, interface or CPAP machine. If a settings update is received and applied, the modem connects a second time to confirm the newly applied settings with the remote service.

In yet another alternative, the information can be transferred via the PC to the WAN by the patient or other user using a removable memory device. The removable memory device is inserted into the CPAP machine to receive the information (compliance data), and then transferred and the inserted into the computer. The information is then uploaded to the computer and uploaded to the remote computer system 15 via the WAN from the PC through its connection to that WAN. Again, this action can be carried out after the user is prompted for example by a message on the computer or on the CPAP machine.

In yet another alternative, the patient is issued with a removable memory device for use with the CPAP apparatus. This can store data from the CPAP apparatus, and can comprise client ID information, device information and/or a download application—as will be described later. When a removable memory device is inserted into the interface of the CPAP apparatus, the removable memory device synchronises any internally stored data and begins recording new data to the memory stick. As part of this, compliance data is transferred to it either automatically or upon prompting by the user. The PC also has a port, into which the memory device is inserted and the compliance data is uploaded to the PC.

Upload to the PC, and subsequent transfer to the centralised computer system 15 can take place upon the user operating suitable software on the PC and/or memory device to facilitate this task. However, in a preferred alternative, the upload and transfer application resides on the removable memory device and activates automatically. The PC contains a memory device detection application. When the application detects that the removable memory device has been inserted into the PC, the upload and transfer application on the memory device is automatically executed, and uploads the data to the PC and facilitates the transfer of that data via the PC/WAN to the centralised computer system. This simplifies the process for the patient, making it more likely that transfer of the data will occur. As an option, the upload application prompts the patient to enter their date of birth or other information as a security check before connecting to and sending the compliance data contained on the memory device to the computer system 15.

Figure 7:
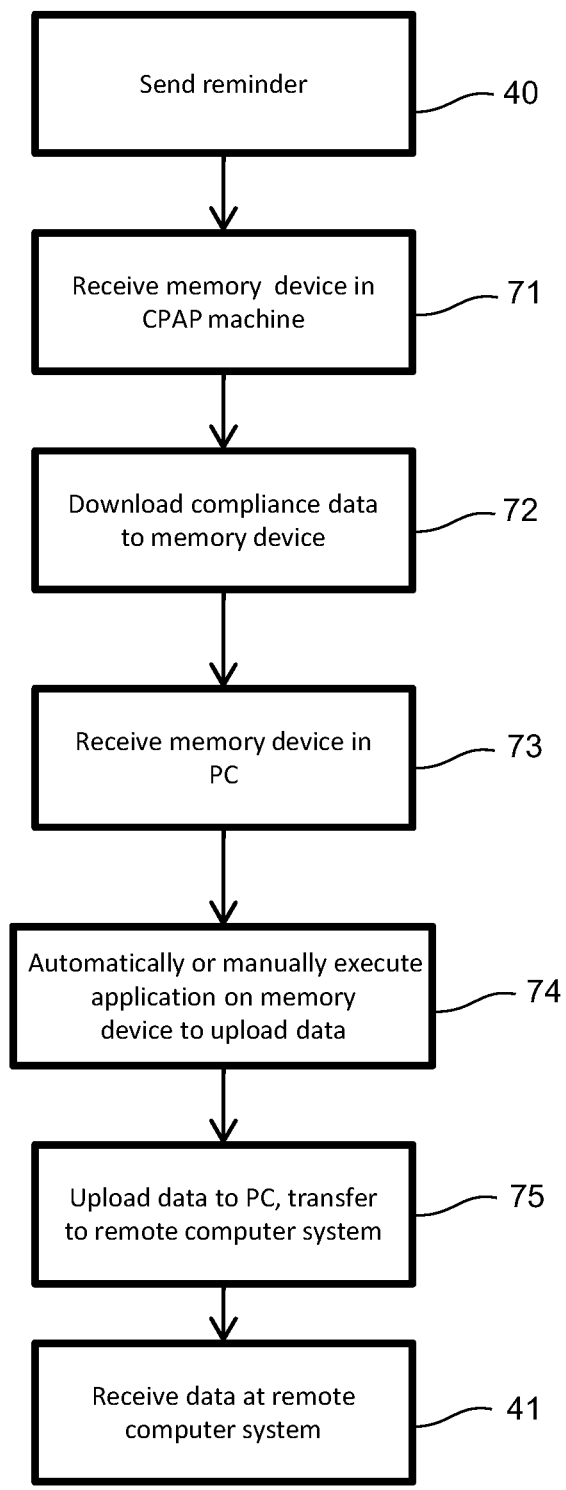
FIG. 7 is a flow diagram showing a method for capturing/sending data via a memory device.

FIG. 7 shows a flow diagram setting out the method for transferring information using a removable memory device. This shows in more detail what occurs between steps 40 and 41 of FIG. 3 when transfer occurs via a removable memory device. The user of their own accord, or upon receiving a reminder through the PC or CPAP apparatus, step 40, plugs the movable memory device into the port of the CPAP apparatus (if not already installed). For example, the patient could receive the reminder as an automated reminder phone call, text, email, message via the PC, CPAP apparatus and/or communications device to remind them to insert their memory stick into their PC to upload the data. Once the memory device is received in the port, step 71, the CPAP apparatus then downloads the information to the memory device, step 72, that includes the compliance, routing and formatting data—either automatically, or upon operation of the CPAP apparatus by the user.

Once the data is downloaded, the user removes the removable memory device and plugs it into the port in the PC, step 73. At this point, in one alternative, when the memory device is received in the port, the PC detects the removable memory device, step 74 and triggers the application on the removable memory device to automatically execute and upload the data to the PC, step 75 and subsequently transfer that data which is received at the remote computer system via the WAN, step 41. To do this, the application on the removable memory device connects to a web service and prompts the patient to enter their date of birth. The patient enters their date of birth, which is sent to the integration engine and checked against their registered date of birth, if the dates match, a message is sent back to the removable memory device application to begin the data upload. On receiving the date of birth confirmation, the remote computer system collects any data files on the removable memory device.

Figure 8:
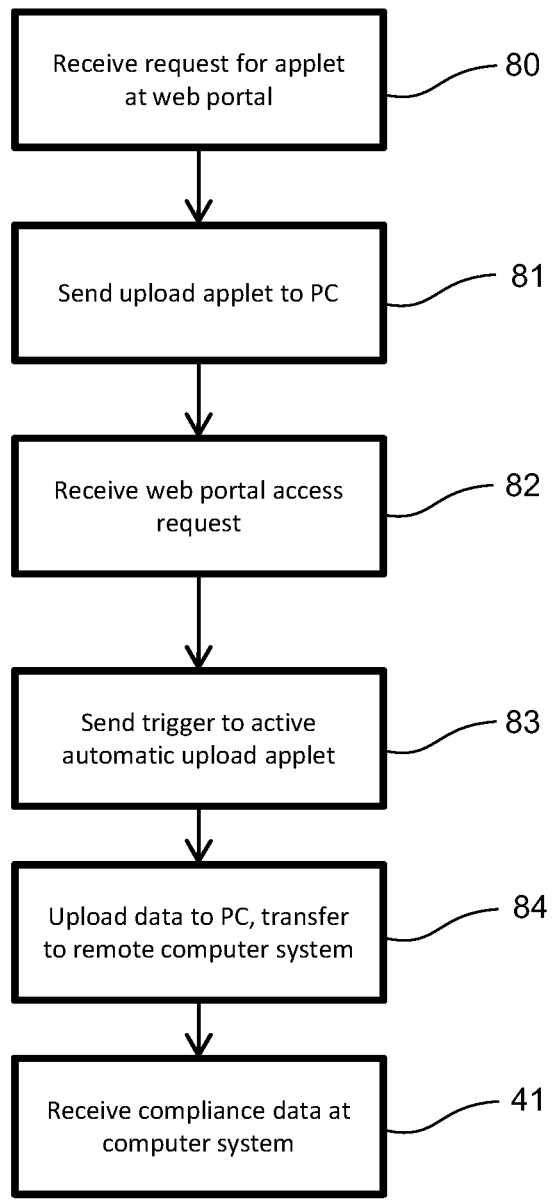
FIG. 8 is a flow diagram showing an alternative method for capturing/sending data.
Figure 9:
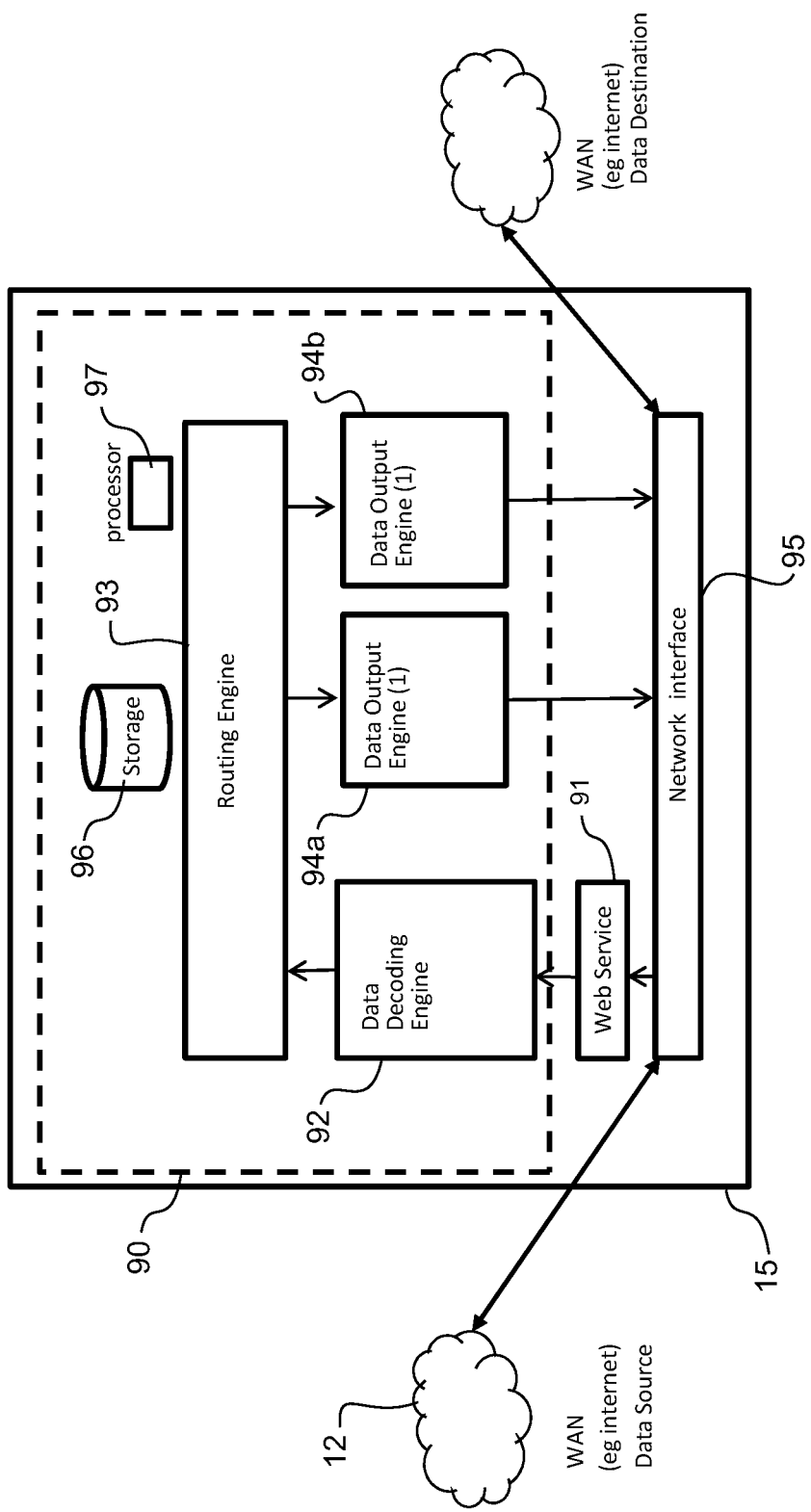
FIG. 9 shows the remote computer system with router functionality.

Referring to FIG. 6 and to the flow chart in FIG. 8, an alternative method for transfer from the removable memory device is described using an upload applet is installed on the PC. In this alternative, the PC, upon user activation, can receive or access a web page/web portal via a browser over the wide area network from the web server. When a user accesses the website (web portal) of the service provider, they can request an upload applet, step 80. This is sent from the web portal server and downloaded to the PC, step 81. When the user accesses the web portal a subsequent time, the web server receives an access request, step 82, and data is downloaded for rendering the web page and also for triggering automatic upload of the data using the applet, step 83. The applet activates automatic upload of compliance data from the removable memory onto the PC and subsequent transfer across to the centralised computer system, step 84. The applet does this immediately if the removable memory device is already in the port, otherwise the applet will await insertion of the removable media device and then transfers the information over the network to the computer system. This compliance data is received at the remote computer system, step 41. In yet another alternative, if the CPAP apparatus is directly or indirectly connected to the PC, the data in a memory of the CPAP apparatus can be automatically uploaded using the applet and transferred. Therefore the upload applet is automatically run on the computer and automatically transfers the data, without user intervention. This simplifies the process for the patient, making it more likely that transfer of the data will occur. The upload applet could, for example, be an ActiveX control that is downloaded from the website and installed by a user. Upon accessing the website, the website can interact with the control to automatic upload information from the CPAP machine to the server and obtain status information Routing Using the Remote Computer System FIG. 9 shows the remote computer system 15 in more detail, and FIG. 10a shows a flow diagram of its operation. In overview, the remote computer system 15 has a data integration engine service 90 that includes a web service 91, a data decoding engine 92, a routing engine 93 and one or more data output engines 94a, 94b. The remote computer system 15 itself has a network interface 95, storage (which includes a database) 96 and a processor 97. In summary, the remote computer system 15 routes the uploaded information to and customises the information for the destination computer system. To do this, the data integration engine receives the information (also termed "input" or "input data") uploaded from the CPAP machine 11 by any suitable method (such as one of those described above). The data integration engine 90 extracts the compliance data from the information, reformats the compliance data in accordance with formatting data for the recipient computer system and then routes the reformatted data to the appropriate recipient computer system 18. The data integration engine is able to receive information (input data) from data sources (such as a CPAP apparatus) in a variety of formats (such as XML or binary), and format that input data to match the requirements of the recipient computer system 18 before forwarding the data.

With reference to FIG. 9 and the flow diagram in FIG. 10a, the remote computer system 15 operation will now be described in more detail. The functionality of the data integration engine 90 and remote computer system 15 generally is operated by the processor 97. Information that is uploaded from the CPAP apparatus 11 is received via the WAN 12 at the network interface 95 and passed to the data decoding engine 92 using the web service 91, step 130. The data decoding engine 92 decodes the information into a common internal data format, step 131, and passes this to the routing engine 93, step 132. Routing rules are stored in the database 96, which are used by the routing engine 93 to format and route information to the appropriate recipient computer system 15. Routing rules (also termed "routing data" or "routing information") are used to define/identify the recipient computer system 18 to which information is to be sent, and to obtain the appropriate output engine to use to send data to the recipient. The appropriate output engine contains the address of the recipient computer system (or the address may be in a database on e.g. a routing system). The routing engine 93 looks up/retrieves the appropriate routing rules for the information in the database 96, step 132, and then dispatches the information in the common internal data format to a data output engine e.g. 94a corresponding to the recipient computer system 18 as indicated by the retrieved routing rules, step 133. Preferably, a separate data output engine e.g. 94a, 94b exists for each recipient computer system 18 (e.g. 18a-18d) to which information is sent. Note, however an output engine might have multiple recipients.

Each data output engine e.g. 94a, 94b includes software modules to transform/encode input data/information from the common data/routing format into the format required by the recipient computer system 18, step 134. The output engines store formatting data which is provided upon creation of the output engines. Such formats, comprise, for example XML, HL7, CSV, ASTM, EDIFACT, HPRIM 2.1, NCPDP, NSF, UB92, X12. Each data output engine e.g. 94a, 94b can customise information for delivery and deliver this information using any sort of suitable transport protocol, such as a web service, ftp, http, e-mail, TCP client, TCP server, fax or a direct database connection. Each data output engine e.g. 94a, 94b has the ability to establish communications with a corresponding recipient computer system 18 and transfer reformatted data to that system. After the data output engine encodes the input data into the recipient computer system format, the data output engine dispatches the encoded information to the recipient computer system via the network interface 95 and WAN, step 135.

The functionality/operation of the routing aspects of the remote computer system 15 will now be described with reference to the flow chart in FIG. 10b, which shows more detail of step 132 of FIG. 10a. A previously described, routing rules are stored in the database 96, which are used by the routing engine 93 to format and route information to the appropriate recipient computer system 15. Three types of routing rules are used, these being:

1) client ID based routing rules,
2) device based routing rules, and
3) default routing rules.

Note, the routing rules are not mutually exclusive and can be combined. Client ID based routing rules are used to format and route information to a recipient (also termed "interested party" or "client") computer system 18 based on the identification of the recipient (client). Device based routing rules are used to format and route information to a recipient computer system 18 based on the CPAP apparatus from which the information originated. Default routing rules are used to route and format information in conjunction to any routing based on the client ID or device ID routing rules. The type of routing rules used will depend on the information uploaded. One or a combination of the three different types of routing rules might be used to identify and dispatch uploaded information to one or more recipient computer systems.

Operation based on client ID based routing rules will now be described in more detail. A client (recipient) is associated with CPAP apparatus used by patients—the client can be associated, for example, by way of being a clinician of the patients, or insurer or dealer providing the CPAP apparatus. Each client (recipient) has a respective recipient computer system (e.g. web server with a web services interface) 18, such as one of those described previously. Client ID based routing rules are stored in a client ID routing table in the database 96, in a format such as that shown in table 4 below. This table stores client IDs allocated to recipients (clients) and associated destination identifier for the appropriate output engine corresponding to the recipient computer systems 18 of those recipients. Each client ID and associated output engine identifier/destination identifier define a routing rule. The client ID is a unique alphanumeric identifier associated with a CPAP apparatus that identifies the recipient (client). The destination identifier can identify an output engine for a respective recipient computer system and/or specify its address. The address for the output engine associated with a recipient computer system address can be termed a "destination address" or a "recipient address". The addresses could take the form of IP addresses, fax numbers, FTP address, and/or email address, for example. The table might also store formatting information for each respective recipient computer system 18.

TABLE 4

| Client ID | Destination identifier |
|---|---|
| 001 | OutputEngine1 |
| 023 | OutputEngine2 |
| 123 | OutputEngine3 |
| 256 | OutputEngine1 |
| 545 | OutputEngine4 |

When a data source (e.g. CPAP apparatus) connects to the integration engine to upload information (step 130 FIG. 10a) it can optionally provide/include a client ID as part of that information. The client ID could be included in a header, for example. On receiving information containing a client ID (FIG. 10b, step 136) the data integration engine 90 retrieves the relevant routing rules for that client ID, steps 137, 138, FIG. 10b. This involves determining if a client ID exists in the information, step 137, and querying a look up table to retrieve any output engines for recipient computer systems associated with that client ID in the database, step 138. The output engine identifier is retrieved for each entry that exists in the table that corresponds to the client ID. Upon retrieving the routing rules, the routing engine dispatches the information to the appropriate data output engine as identified in the rule e.g. 94a, 94b for the destination, step 133, FIG. 10a. The data output engine formats the information into a suitable format (such as CSV) according to the formatting information contained in the output engine, step 134, FIG. 10a. The data output engine then dispatches/routes the formatted information to the identified recipient computer system 18 using the address/identifier, step 135, FIG. 10a.

Figure 10B:
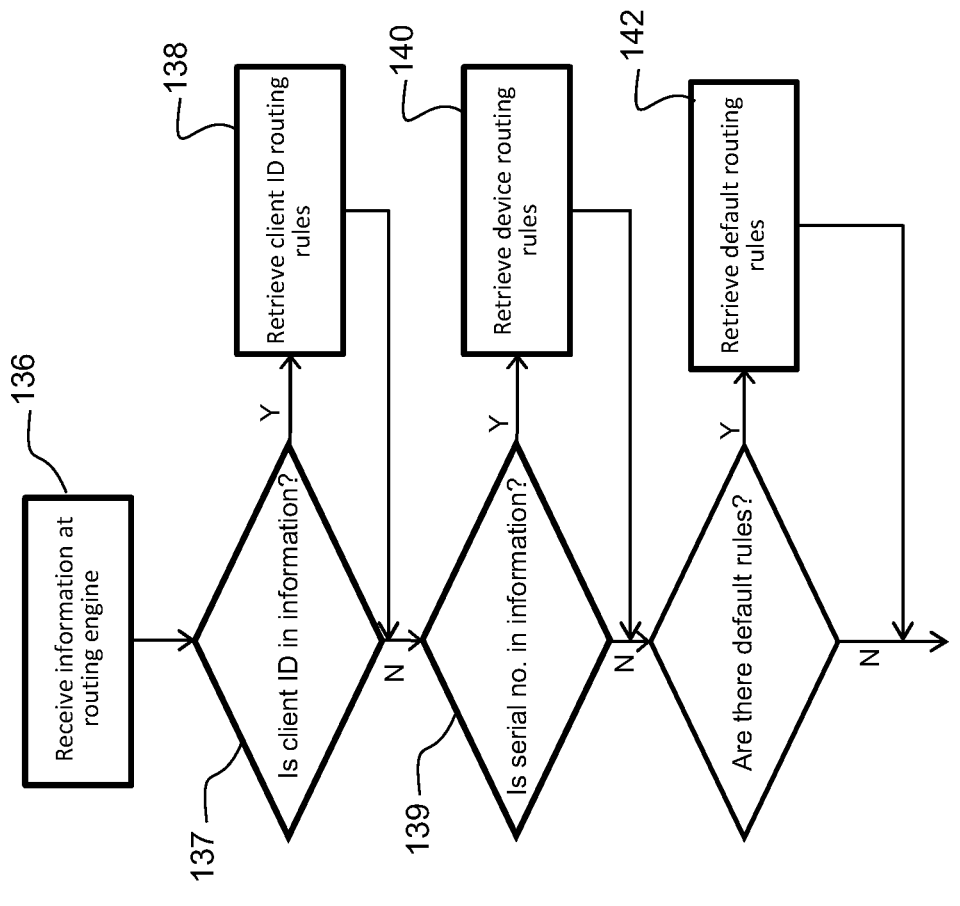
FIGS. 10a, 10b are a flow diagrams showing routing of compliance information to different interested parties.
Figure 10A:
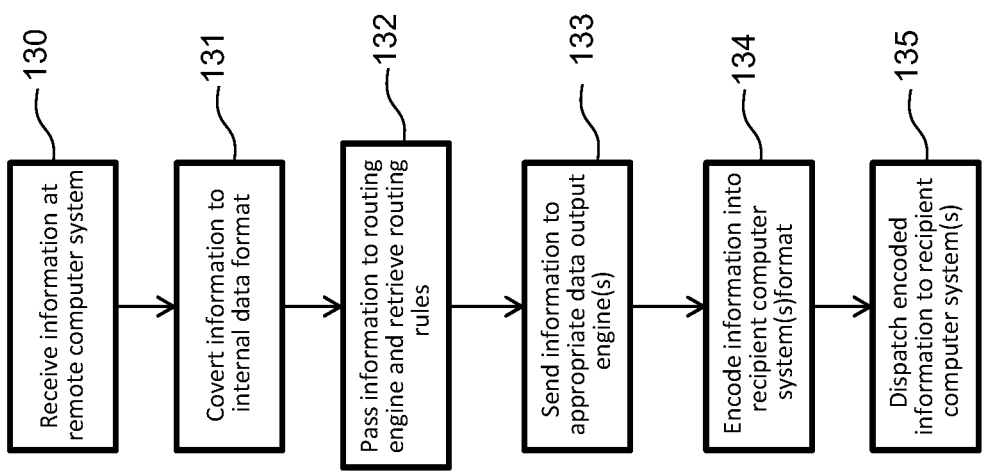

Referring to FIGS. 10a and 10b, an example of routing based on client ID rules will be described with reference to table 4. A client (recipient) is assigned a client ID of "123". Information (in the form of e.g. binary files) is uploaded from one of the CPAP apparatus, step 130. In addition to compliance data, the information includes the client ID 123 of the client associated with that CPAP apparatus 11. Information could be uploaded in any manner previously described. Upon receiving the information at the network interface 95, step 130, it is passed to the web service 91 and on to the data decoding engine 92. The data decoding engine decodes the binary files into a common internal format (such as XML), step 131, and the data, along with the client ID 123 is then passed to the routing engine 93, step 132. When the information reaches the routing engine, to find the client ID based routing rules, the routing engine accesses the routing rules database 96 and checks to see if any entries exist for an associated output engine (relating to a recipient computer system) corresponding to the client ID 123, step 138. In this case the output engine is OutputEngine1. The data output engine e.g. 94a identified receives the information, step 133, and transforms the information into a suitable format (such as CSV), step 134, using formatting information, and delivers it to the recipient computer system 18 over a SOAP web service, step 135.

Operation based on device (apparatus) based routing rules will now be described in more detail. A patient is issued with a breathing apparatus (e.g. CPAP apparatus) 11 by their health care provider, insurer or dealer and is registered in a patient management system. A routing rule for a particular CPAP apparatus 11 is then able to be created by registering the apparatus on the system. Registration involves providing a device serial number and an associated recipient computer system destination address to the data integration engine 90, via a web service API or registration web site. To do this, on registering a patient, a client's patient management system makes a web service call to the data integration engine 11 to register the patient in the system. The call includes the CPAP apparatus serial number, the patient's date of birth, and a username and password for security. On receiving the call, the data integration engine 90 validates the username and password, looking up the destination identifier associated with the username/password from a client table. An entry is then added to the registration routing table. As a result, the data integration engine 90 stores serial numbers for each patient CPAP apparatus 11 and associated destination identifiers for the data output engine corresponding recipient computer systems 18 of those interested parties who provided the CPAP apparatus. The information is stored in the database 96, in a table such as that shown in table 5. This information is stored along with corresponding dates of birth for the patients associated with each device. The serial numbers, along with the respective output engine identifiers form routing rules. The table might also store formatting information for each respective recipient computer system 18.

TABLE 5

| Ser. No. | Date of Birth | Destination |
|---|---|---|
| 123,456 | Aug. 26, 1973 | OutputEngine1 |
| 123,457 | Sep. 24, 1968 | OutputEngine2 |
| 234,568 | Oct. 12, 1959 | OutputEngine1 |
| 232,323 | Jul. 01, 1940 | OutputEngine3 |

Referring to FIGS. 10a, 10b, when a data source (e.g. CPAP apparatus) connects to the data integration engine 90 to upload information, it can optionally provide a serial number as part of that information. On receiving information containing a serial number, step 130, the data integration engine retrieves the relevant routing rules for that serial number, step 132. This involves determining whether the information contains a serial no, step 139, and if so, querying a look-up table to retrieve the output engine capable to output data to any recipient computer systems 18 associated with that serial number in the database, step 140. The output engine identifier is retrieved for each entry that exists in the table that corresponds to the serial number. Upon retrieving the routing rules, the routing engine dispatches the information to the appropriate data output engine for the destination, step 133. The data output engine, e.g. 94*a*, 94*b* identified receives the information, step 133, and formats/transforms the information into a suitable format (such as CSV) according to the formatting information, step 134. The data output engine then dispatches/routes the formatted information to the associated recipient computer system 18, step 135.

An example of routing based on device (apparatus) based routing rules will be described with reference to table 5. A CPAP apparatus 11 has the serial number 123456. Information (in the form of e.g. binary files) is uploaded from the CPAP apparatus, step 130. In addition to compliance data, the information includes the serial number 123456 of that CPAP apparatus. Information could be uploaded in any manner previously described. Upon receiving the information at the network interface 95, step 130, it is passed to the web service and on to the data decoding engine 92. The data decoding engine decodes the binary files into a common internal format (such as XML), step 131, and the data, along with the serial number 123456 is then passed to the routing engine 93, step 132. When the information reaches the routing engine, to find the device based routing rules, the routing engine accesses the routing rules database and checks to see if any entries exist for an output engine corresponding to the serial number 123456, steps 139, 140. In this case the output engine is OutputEngine1. The data output engine e.g. 94*b* identified receives the information, step 133, and transforms the information into a suitable format (such as CSV), step 134, and delivers it to the recipient computer system 18 over a SOAP web service, step 135.

Operation based on default routing rules will now be described in more detail. A default routing rule is a global rule that can be associated with one or many destinations, and is able to define a secondary destination for the data. Default routes allow data for one or many destinations to also be forwarded on to a second destination. Default routing rules are stored in a default routing table. This table stores the destination address/identifier and any corresponding alternative destination(s) in the database 96. These form routing rules.

TABLE 6

| Destination | Alternate route |
|---|---|
| OutputEngine1 | OutputEngine2 |
| OutputEngine1 | OutputEngine3 |
| OutputEngine4 | OutputEngine5 |
| OutputEngine6 | OutputEngine7 |

On receiving information the routing engine 93 retrieves routing rules for a destination using a client ID or device serial number as described above, steps 137-140. The routing engine will also check this default routing table, step 141, to see if there are any alternative output engines specified, and if so, retrieve them step 142. The routing engine 93 will also dispatch the information to any alternative destinations specified by the default routing rules. It does this by sending the information to the identified data output engine, e.g. 9*a*, 94*b*, step 133, which converts the information to the recipient format, step 134 and dispatches the information to the alternative recipient computer system 18, step 135. A data output engine can be configured to dispatch information to more than one server.

Reminder Server

Figure 11:
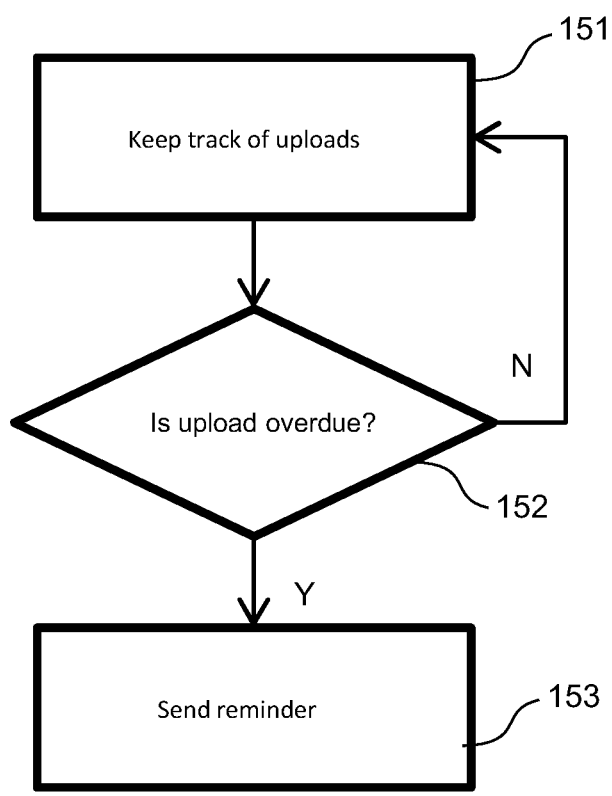
FIG. 11 is a flow diagram showing the reminder server operation.

FIG. 11 is a flow chart showing operation of the reminder server 150. The reminder server receives the information uploaded to the remote computer system, step 151. The reminder server can determine how long has passed since the last upload of information. If too long has passed, step 152, the reminder server generates a reminder that can be communicated to the patient to ensure they upload the data from the CPAP machine, step 153. The reminder server can also determine whether the patient is complying with a treatment regime. Messages can be communicated to the user to assist them to reach compliance. The reminder and compliance message could be communicated in one of various ways. For example, it might be a recorded message/automated telephone call, text message, email or similar via the PC, landline or mobile telephone or other communications device. Alternatively, the patient might receive a reminder/compliance message when they access the service provider's website. Alternatively, a reminder/compliance message could be communicated to the CPAP machine and displayed to the user. Instead of communicating with the remote computer system 15, the reminder server 150 can communicate with a recipient computer system e.g. 19*a*. The reminder server contains and/or is coupled to and/or can control the required hardware (e.g. telephone, computing device, transmission device and/or communications network or the like) to communicate the reminder via the desired means as mentioned above. There could be a separate reminder system for each mode of communication, or a single reminder system that is configured to and/or contains operate required hardware to communicate via any of the desired modes. In FIG. 2*a*, the reminder system is shown as a single entity for clarity purposes—but it will be appreciated that the configuration depicted is not necessarily the actual or only possible reminder system configuration.

The service provider or other appropriate party is able to configure if a patient is to receive automated reminders, how they should receive those reminders and the cycle at which they are to receive reminders. This is done when a patient is set up in the system. By default, preferably there are two reminder cycles available as follows.

Basic reminder cycle in which the reminder server 150 will automatically contact (or facilitate contact) of the patient via the selected contact methods (e.g. telephone, voice/text message, email) at 7, 14. 30, 60 and 90 days (or other suitable interval) to remind them to upload their clinical data.

Advanced reminder cycle in which the reminder server 150 will, in addition to the contacts made in the basic cycle, contact a patient at 180 days and 1 year (or other suitable interval) to remind them to upload their clinical data.

The automated telephone call reminder system 150 is able to place an automated phone call to a patient, at a scheduled time using the reminder server 150 controlling a telephone device. The calls are calibrated based on a patient's time zone (selected when a patient is created in the system) to only place calls between a suitable hour, such as between 8:00 am and 9:00 pm. When a call is answered, the reminder system waits 2 seconds (or other suitable period) to determine if a patient or answering machine has answered the call. If an answering machine recording is detected to be triggered within that 2 second window, a message is placed to remind the patient to upload the data at their convenience. If the call is answered by a patient a recording instructs them to upload their data e.g. by inserting the memory card from their CPAP apparatus, into an internet connected computer, and following the onscreen instructions. Clearly, instructions provided will match the manner that it is expected the user will use to upload data. If the call is not answered by either a patient or answering machine, the system will try again for 3 consecutive days (or other suitable period.) If a data upload has been made within 2 days of a scheduled call, the call will not be made. The reminder system 150 preferably includes a default voice for the telephone messages, although a provider can override this with their own recordings by uploading new voice audio files through a web interface.

The text message (e.g. SMS) reminder system 150 is able to place a text message to a patient's mobile device (e.g. cellular telephone) to remind them to upload their clinical data. The text messages are calibrated based on a patient's time zone (selected when a patient is created in the system) to only occur between a suitable time, such as 8:00 am and 9:00 pm. The default text message asks the user to upload their clinical data, and instructs them on how to do this. If a data upload has been made within 2 days of a scheduled text message, the call will not be sent.

The system includes a default message for text messages; however a provider can override this with their own message through a web interface.

The E-mail message reminder system 150 is able to send an email message to a patient to remind them to upload their clinical data. The default email message asks the user to upload their clinical data, and instructs them on how to do this. If a data upload has been made within 2 days of a scheduled email, the email will not be sent. The system includes a default message for e-mail messages; however a provider can override this with their own message through a web interface.

Other modes of communicating a reminder could be envisaged by those skilled in the art and the reminder server is not restricted to only the communication modes mentioned above. These are provided by way of example only.

The reminder system 150 may also be used to remind the patient about other events such as returning a modem (GSM or telephone) back to their provider. During a call the system may also be used to gain feedback from the patient about how comfortable their treatment is, if they are having any treatment problems or if they would like to be personally contacted by their healthcare provider.

What is claimed is:

1. A compliance system for routing breathing apparatus compliance data from a plurality of breathing apparatus devices to a plurality of recipient computer systems, the system comprising:
a network interface and a processor configured to receive input data, via a network, from a plurality of breathing apparatus devices, the input data including breathing apparatus compliance data and routing information, wherein the compliance data comprises a plurality of different formats and the routing information includes one or both of a client ID or a device serial number;
the processor configured to execute a data integration engine configured to receive the input data from the network interface, the data integration engine including a data decoding engine, a routing engine, and a plurality of data output engines, each of the plurality of data output engines comprising software modules; and
a memory storage device configured to store a routing rules database, wherein the routing rules database comprises routing rules that include one or more of:
client ID based routing rules,
device serial number based routing rules, or
default routing rules configured to identify alternative destinations,
wherein the data decoding engine is configured to decode the compliance data from the plurality of different formats in binary files into a text based common internal data format and pass the compliance data in the common internal data format and the routing information to the routing engine,
wherein the routing engine is configured to:
receive the compliance data in the common internal data format and the routing information,
determine one or both of the client ID or the device serial number from the received routing information,
retrieve one or a combination of the routing rules according to the received input data, wherein the routing rules retrieved and used by the routing engine depends on the received compliance data and routing information,
identify at least a first data output engine for a first one of the recipient computer system and a second data output engine for a second one of the recipient computer systems from the plurality of data output engines and destination identifiers associated with the first and second data output engines, respectively, from the routing rules database using the retrieved one or a combination of the routing rules, wherein the routing engine determines which of the breathing apparatus compliance data to be sent to the first data output engine and which of the breathing apparatus compliance data to be sent to the second data output engine based on one or more of an application of the client ID based routing rules using the determined client ID, an application of the device serial number based routing rules using the determined device serial number, or an application of the default routing rules on the breathing apparatus compliance data; and
send breathing apparatus compliance data in the common internal data format to the identified at least first and second data output engines, wherein the routing engine uses the retrieved one or a combination of the routing rules to send at least some of the breathing apparatus compliance data to the first one of the recipient computer systems and at least some of the breathing apparatus compliance data to the second one of the recipient computer systems, wherein each of the plurality of data output engines include instructions to establish communication with its corresponding recipient computer system;
and for each of the at least first and second data output engines identified, the identified data output engines are configured to:
receive the compliance data in the common internal data format,
retrieve formatting data specific to a recipient computer system associated with a respective data output engine, wherein the at least first and second recipient computer systems have different data format requirements, reformat the compliance data based on the formatting data wherein the reformatted compliance data is customized for delivery using a transport protocol acceptable to the recipient computer system associated with the respective data output engine, and transmit the reformatted compliance data to the recipient computer system associated with the respective data output engine.

2. The computer system of claim 1, wherein the at least first and second data output engines each comprises one or more software modules configured to be executed by one or more hardware processors.

3. The computer system of claim 1, wherein each recipient computer system is operated by or on behalf of a service provider, an interested party, or both, the service provider or the interested party comprising one or more of:

an insurance company,
a medical equipment dealer,
healthcare professionals, or
a patient.

4. The computer system of claim 3, wherein each recipient computer system comprises one or more of a database, reporting tool, or user terminal being operated by or on behalf of one or more of a service provider or interested parties.

* * * * *